United States Patent [19]

Albal et al.

[11] Patent Number: 4,975,266
[45] Date of Patent: Dec. 4, 1990

[54] PRODUCTION OF HYDROGEN PEROXIDE

[75] Inventors: Rajendra S. Albal; Robert N. Cochran, both of West Chester; Lawrence M. Candela, Philadelphia, all of Pa.

[73] Assignee: Arco Chemical Technology, Inc., Wilmington, Del.

[21] Appl. No.: 457,662

[22] Filed: Dec. 27, 1989

Related U.S. Application Data

[63] Continuation-in-part of Ser. No. 295,409, Jan. 10, 1989, Pat. No. 4,897,252.

[51] Int. Cl.⁵ .................. C01B 15/026; C07C 45/32
[52] U.S. Cl. .................................... 423/591; 568/320
[58] Field of Search ..................... 423/591; 568/320

[56] References Cited

U.S. PATENT DOCUMENTS 2,819,949  1/1958  Keeler et al. .................. 423/591
2,871,104  1/1959  Rust ............................. 423/591

FOREIGN PATENT DOCUMENTS 785211  5/1968  Canada ........................... 423/591
758967  10/1956  United Kingdom ............. 423/591

Primary Examiner—Wayne A. Langel
Attorney, Agent, or Firm—William C. Long

[57] ABSTRACT

Hydrogen peroxide is produced by liquid phase molecular oxygen oxidation of methyl benzyl alcohol. Inhibiting impurities are removed prior to oxidation.

6 Claims, 1 Drawing Sheet

PRODUCTION OF HYDROGEN PEROXIDE

RELATED APPLICATIONS

This application is a continuation-in-part of copending application Ser. No. 07/295,409 filed Jan. 10, 1989, U.S. Pat. No. 4,897,252.

BACKGROUND OF THE INVENTION

1. Field of the Invention

The present invention relates to the production of hydrogen peroxide by the oxidation of methyl benzyl alcohol.

2. Description of the Prior Art

Hydrogen peroxide is an important chemical of commerce which is produced in very large quantities for use in a number of industrial applications. The predominant process used commercially for the production of hydrogen peroxide involves the oxidation of anthrahydroquinone, extraction of hydrogen peroxide and reduction of the resulting anthraquinone to anthrahydroquinone which is reused. This process requires very high capital expenditures in that use of a working solvent with efficient recycle of various process components is necessary.

Substantial efforts have been directed to processes which involve direct combination of hydrogen and oxygen but thus far such processes have not found widespread success.

Hydrogen peroxide has been formed by the oxidation of secondary alcohols. At one time the production of hydrogen peroxide by oxidation of isopropanol was practiced commercially. Other secondary alcohols which have been mentioned as possible starting materials for hydrogen peroxide production include methyl benzyl alcohol and cyclohexanol. See, for example, U.S. Pat. Nos. 2,871,102, 2,871,103, and 2,871,104 of Shell Development.

Hydrogen peroxide has also been formed by oxidation of high boiling secondary alcohols such as diaryl methanol, the product hydrogen peroxide being stripped from the reaction mixture during oxidation; see U.S. Pat. No. 4,303,632.

In certain commercial technologies, substantial quantities of various secondary alcohols are produced. For example, in the coproduction of propylene oxide and styrene monomer by hydroperoxide epoxidation, methyl benzyl alcohol, which is also referred to as alpha phenyl ethanol, 1-phenyl ethanol or methyl phenyl carbinol, is formed and ultimately converted by dehydration to styrene monomer. See U.S. Pat. No. 3,351,635.

The present invention provides a process where commercial streams containing methyl benzyl alcohol can be employed effectively and efficiently for hydrogen peroxide production.

SUMMARY OF THE INVENTION

In accordance with the invention, an improved process for the production of hydrogen peroxide by oxidation of methyl benzyl alcohol is provided. In particular, the process of this invention involves the production of hydrogen peroxide by molecular oxygen oxidation of methyl benzyl alcohol in the liquid phase wherein contaminating impurities which inhibit the hydrogen peroxide production are removed or are converted to non-inhibiting materials prior to oxidation. Acetophenone is a coproduct.

BRIEF DESCRIPTION OF THE DRAWING

The accompanying

DETAILED DESCRIPTION OF THE INVENTION

Figure 1:
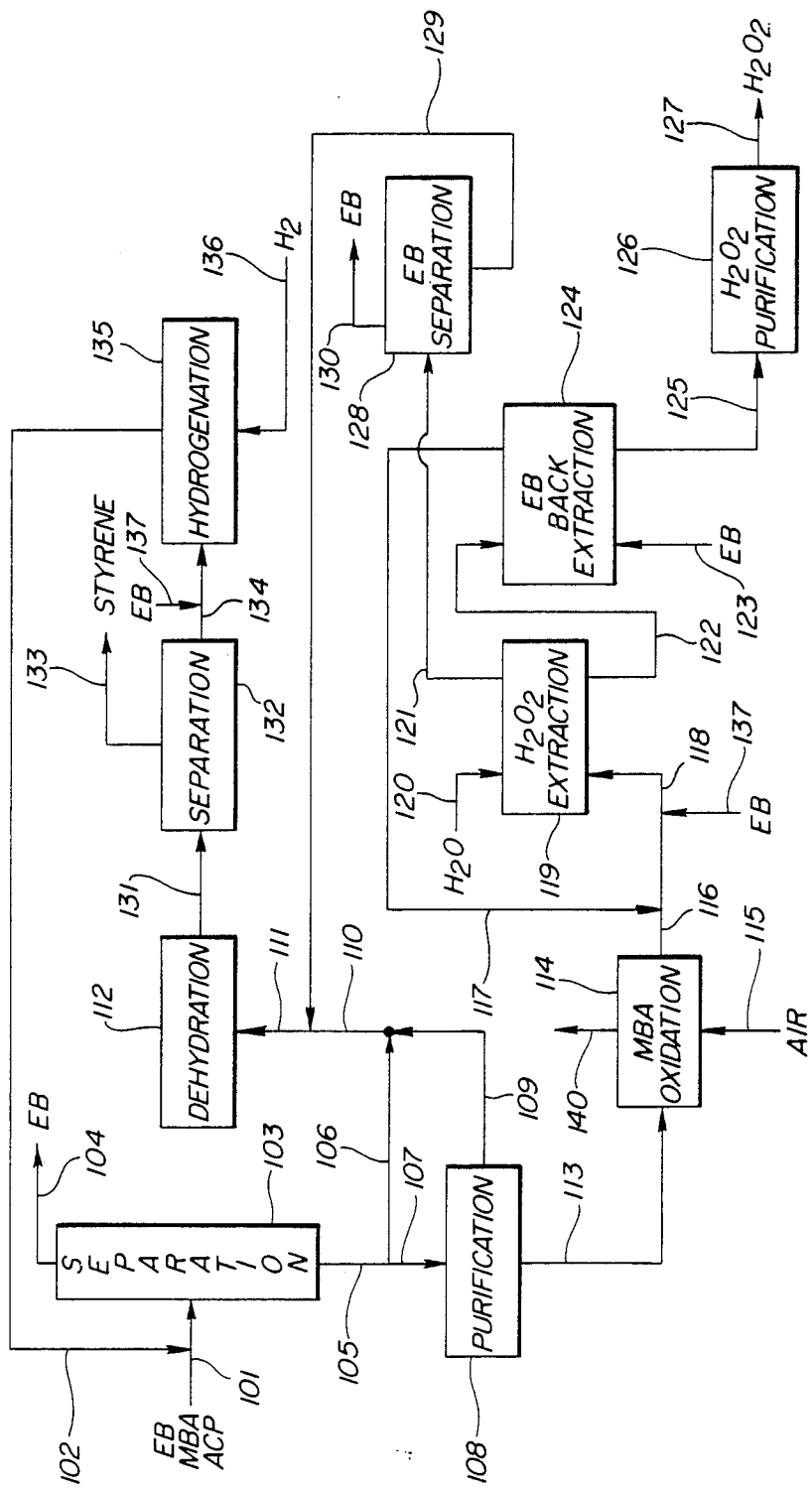
FIG. 1 illustrates in schematic form a suitable embodiment of the invention.

Commercially available sources of methyl benzyl alcohol, for example, methyl benzyl alcohol process streams which are produced in the coproduction of propylene oxide and styrene monomer, contain contaminants which seriously interfere with oxidation to hydrogen peroxide. In accordance with the present invention, these contaminants are removed or converted to non-inhibiting materials prior to oxidation and production of hydrogen peroxide.

In accordance with the present invention, methyl benzyl alcohol is oxidized in the liquid phase with molecular oxygen at elevated temperatures and pressure with the concentration of water in the reaction mixture maintained below 4% by weight, preferably below 2% by weight and most preferably below 1% by weight. In this way high reaction rates and selectivities to hydrogen peroxide can be achieved.

In an especially preferred embodiment of the invention, hydrogen peroxide production can be integrated with the production of propylene oxide and styrene monomer by epoxidation with ethyl benzene hydroperoxide. In this embodiment, feed to the methyl benzyl alcohol oxidation comprises a methyl benzyl alcohol/acetophenone process stream from the propylene oxide and styrene monomer process as will be hereinafter described.

The oxidant which is used in the present invention is molecular oxygen. It is a convenient source of the oxygen although pure oxygen, oxygen-enriched air, oxygen diluted with various inerts such as argon, carbon dioxide and the like can be used.

The conditions of temperature and pressure are such as to maintain the reaction mixture in the liquid phase. Elevated temperatures ranging from about 100°–250° C., preferably 120°–180° C., are employed to achieve reasonable reaction rates.

It is important to provide substantial partial pressures of oxygen sufficient to maintain reasonable reaction rates. A preferred range is 15 to 250 psi partial pressure of oxygen in the feed gases, with a broader useful range being 0.5 to 1000 psi.

Total pressure in the reaction zone should be sufficient to maintain the reaction mixture in the liquid phase. Generally, pressures in the range of 5 psig to 1000 psig are useful.

Metal contaminants and other materials which promote peroxide decomposition are to be avoided in the reaction zone. Known peroxide stabilizers such as pyrophosphates are useful and can be employed.

The oxidation of methyl benzyl alcohol to hydrogen peroxide and acetophenone is an exothermic reaction which requires removal of the heat of reaction. This can be accomplished, for example, by circulating a portion of the reaction mixture through indirect cooling means. Alternatively, the heat can be removed by boil-up and condensation of components of the reaction mixture.

Essential to practice of the invention is the maintaining of low water concentrations in the liquid reaction mixture, i.e. water concentration below 4 wt. %, preferably below 2 wt. % and most preferably below 1 wt. % water in the reaction mixture.

Water concentration can be controlled in a number of ways. In the first instance, the water content of the various feed materials is appropriately kept to a minimum. In batch or continuous systems, water can be removed as a vapor from the reaction zone, for example, along with nitrogen, unreacted oxygen and various other components of the reaction mixture. Whereas in conventional systems this water is condensed and refluxed to the reaction zone, in practice of the present invention the water removed as vapor is not returned to the reaction zone thus preventing build-up of substantial concentrations of water in the reaction mixture. In conjunction with this procedures, or as an alternative thereto, liquid reaction mixture can be removed, hydrogen peroxide and water can be separated therefrom and the remaining components further processed or recycled.

The invention can be further described with reference to the attached drawing which illustrates in schematic form an especially preferred embodiment. Referring to the drawing, a process stream from a commercial process for propylene oxide/styrene monomer coproduction comprised mainly of methyl benzyl alcohol, acetophenone and ethyl benzene in line 101 is combined with a methyl benzyl alcohol stream in line 102 from acetophenone hydrogenation and passed to distillation zone 103.

By conventional distillation ethyl benzene is separated overhead via line 104 for recycle to the propylene oxide/styrene monomer process. A higher boiling stream mainly comprised of methyl benzyl alcohol and acetophenone and containing small amounts of phenol and ethyl phenols is separated from distillation zone 103 through line 105.

A portion of the methyl benzyl alcohol and acetophenone stream passes via lines 106, 110 and 111 to dehydration zone 112. The remaining portion of this stream passes via line 107 to purification zone 108.

It has been found in accordance with the present invention, that certain compound such as phenol and ethyl phenols which are usually present with methyl benzyl alcohol in commercial streams severely inhibit the molecular oxygen oxidation of methyl benzyl alcohol to hydrogen peroxide and acetophenone. Accordingly, the methyl benzyl alcohol and acetophenone stream from distillation zone 103 is first treated in purification zone 108 to remove materials which inhibit methyl benzyl alcohol oxidation or to convert these materials to non-inhibitive compounds.

Preferably, purification zone 108 comprises both distillation and caustic and/or ion exchange treatment. By distillation, ethyl phenols can be separated as high boiling material from methyl benzyl alcohol and acetophenone. Basic ion exchange resins such as poly(vinylpyridine) resins can be employed to separate the phenols as described, for example, in Sumitomo Japanese Patent Publication 39025 of 1981. Caustic treatment is effective to remove phenol.

From purification zone 108, the methyl benzyl alcohol/acetophenone stream passes via line 113 to oxidation zone 114 wherein the methyl benzyl alcohol is reacted with molecular oxygen to form hydrogen peroxide and acetophenone. As shown, the molecular oxygen is provided by air introduced via line 115.

Conditions of temperature and pressure are maintained in zone 114 effective to maintain the reaction mixture in the liquid phase and to maintain high reaction rate and selectivity to hydrogen peroxide and acetophenone. The water content of the reaction mixture is maintained below 4 wt. %, preferably below 2 wt. % and most preferably below 1 wt. % by stripping water formed during the oxidation out of the reaction mixture with unreacted oxygen and inert gases via line 140.

Liquid reaction mixture which contains product hydrogen peroxide passes from 114 via line 116 and is processed for the recovery of the hydrogen peroxide. In an especially preferred practice as describe din detail in copending application Ser. No. 07/295,411, filed Jan. 10, 1989, ethyl benzene extraction is used in the separation of the oxidate mixture. The disclosure of said copending application is incorporated herein by reference.

The oxidate is admixed with ethyl benzene introduced via line 137 and with an ethyl benzene extraction mixture from back extraction extractor 124 via line 117. The mixture passes to tower extractor 119 and flows countercurrent to water which is introduced via line 120.

The organic phase comprised of ethyl benzene, methyl benzyl alcohol and acetophenone passes via line 122 to distillation zone 128. The aqueous hydrogen peroxide phase passes via line 122 to extractor 124 wherein small amounts of contained methyl benzyl alcohol and acetophenone are extracted with ethyl benzene introduced via line 123. The organic phase is removed via line 117 and recycled to admixture with oxidate from reactor 114.

The aqueous hydrogen peroxide phase passes via line 125 to purification zone 126 from which the final purified hydrogen peroxide is recovered via line 127.

In separation zone 128, ethyl benzene is separated overhead and can be recycled to admixture with oxidate form reactor 114 via lines 130 and 137.

Advantageously, the methyl benzyl alcohol and acetophenone stream passes via line 129 to integration with a commercial propylene oxide/styrene monomer process, as shown. The methyl benzyl alcohol and acetophenone pass via line 129 and are admixed with a comparable stream from separation zone 103 via lines 105, 106 and 110 and passed to dehydration zone 112 wherein methyl benzyl alcohol is dehydrated to styrene monomer. Dehydration effluent is transferred via line 131 to zone 132 wherein product styrene monomer is recovered and removed via line 133.

The remaining mixture of unconverted methyl benzyl alcohol and acetophenone is admixed with ethyl benzene introduced via line 137 and passed via line 134 to zone 135 wherein acetophenone is hydrogenated to methyl benzyl alcohol. The effluent stream from 135 is recycled via 102 to separation zone 103 and thus re-integrated into the process.

The following examples illustrate the practice of the invention. Unless otherwise stated, units are parts by weight per hour and percentages are weight percent.

EXAMPLE 1

Referring to the drawing, 1000 parts of a mixture comprised of 65% ethyl benzene, 29% methyl benzyl alcohol and 6% acetophenone in line 101 is combined with 314.5 parts of a 52% ethyl benzene, 43% methyl benzyl alcohol and 5% acetophenone stream from line 102 and passed to distillation zone 103. About 651 parts of ethyl benzene are recovered overhead and recycled via line 104 to the ethyl benzene oxidation of a propylene oxide/styrene monomer process.

The bottom stream comprised of approximately 84% methyl benzyl alcohol and 16% acetophenone and containing 1200 ppm phenol and 1600 ppm 2, 3 and 4 ethyl-phenols is divided into two streams—90 parts passing via lines 106, 110 and 111 to dehydration zone 112 and 411 parts passing via line 107 to purification zone 108.

In zone 108 the oxidation inhibiting phenols are separated by distillation. Suitable conditions are an overhead pressure of 40 torr, overhead temperature of 116° C. and bottom temperature of 135° C. About 205.5 parts of the bottoms, phenols-rich stream, comprised of approximately 84% methyl benzyl alcohol and 16% acetophenone and containing the predominance of the ethyl-phenols is sent via lines 109, 110 and 111 to dehydration zone 112. About 205.5 parts of a phenols-lean stream, comprised of approximately 84% methyl benzyl alcohol and 16% acetophenone is sent via line 113 to oxidation reactor 114.

Conditions in the oxidation reactor are 140° C. and 300 psig; 66 parts of air are sparged into the reactor. Oxygen partial pressure in the vent gas exiting via line 140 is 16 psia. Methyl benzyl alcohol conversion in the reactor is 30% with $H_2O_2$ selectivity about 80%. About 217.5 parts of liquid reaction mixture comprised of 55.4% methyl benzyl alcohol, 38.6% acetophenone, 5.3% $H_2O_2$ and 0.7% $H_2O$ are removed via line 116, admixed with 178 parts pure ethyl benzene from line 137 and 56 parts of an ethyl benzene recycle stream in line 117 from the ethyl benzene back extraction unit 124, comprised of 98.0% ethyl benzene, 1.7% methyl benzyl alcohol, 0.1% $H_2O$ and 0.2% acetophenone. The combined feed to the $H_2O_2$ extractor in line 118 is 448 parts, comprised of 51.5% ethyl benzene, 26.9% methyl benzyl alcohol, 18.7% acetophenone, 2.6% $H_2O_2$ and 0.3% $H_2O$.

About 35 parts water is fed to the extractor via line 120. The heavier aqueous product from the extractor exits via line 122; it is about 45 parts, comprised of approximately 25.6% $H_2O_2$, 3% methyl benzyl alcohol and 0.5% acetophenone. The lighter organic product from the extractor exits via lines 121 to the ethyl benzene separation zone 128. This stream is about 438 parts, comprised of about 52.6% ethyl benzene, 27.5% methyl benzyl alcohol, 19.1% acetophenone, 0.7% $H_2O$ and 0.015% $H_2O_2$.

The organics in the aqueous product from the $H_2O_2$ extractor are recovered by back extraction with ethyl benzene in extractor 124. About 52.4 parts ethyl benzene are fed to 124 via line 123. The light organic product exits via line 117 and is sent back to be mixed with the organic feed to the $H_2O_2$ extractor 119. The heavy aqueous product exits via line 125 and is sent to $H_2O_2$ purification zone 126; it is about 43.4 parts, comprised of 25.5% $H_2O_2$ and 0.03% methyl benzyl alcohol and 73.4% water.

Trace organics are separated in $H_2O_2$ purification section 131, and the peroxide product is concentrated, if desired, by evaporation of water (not shown).

The organic product from the $H_2O_2$ extractor is sent to ethyl benzene separation 128 via line 121. This stream is about 438 parts comprised of 52.6% ethyl benzene, 27.5% methyl benzyl alcohol, 0.7% $H_2O$ and 19.1% acetophenone. The overhead ethyl benzene stream in amount of 230.6 parts is recovered in line 130 and recycled to $H_2O_2$ extraction 119 and ethyl benzene back extraction 124. About 3.1 parts water is also removed (not shown) in Unit 128. The bottoms stream 129 is about 204.5 parts, comprised of 59% methyl benzyl alcohol and 41% acetophenone.

The combined streams in lines 110 and 129 in amount of 500 parts and comprised of 74% methyl benzyl alcohol and 26% acetophenone is dehydrated in zone 112. About 95% conversion of methyl benzyl alcohol to styrene occurs in 112, resulting in a product stream in line 131 of 500 parts comprised of 4% methyl benzyl alcohol, 26% acetophenone, 60% styrene and 10% water. Styrene separation unit 132 separates 300 parts styrene in line 133 and 51 parts water (not shown). The other product exits line 134 and is 149 parts, comprised of 12% methyl benzyl alcohol and 88% acetophenone. This is diluted with 163.5 parts ethyl benzene in line 137 and sent to acetophenone hydrogenation unit 135.

About 90% of the acetophenone fed to hydrogenation is converted by reaction with 2.1 parts hydrogen from line 136. The product stream in amount of 314.5 parts is recycled back to propylene oxide/styrene monomer refining section 103 and is comprised of 52% ethyl benzene, 43% methyl benzyl alcohol and 5% acetophenone.

EXAMPLE 2

A synthetic feed stream corresponding to the composition of a typical methyl benzyl alcohol oxidation feed stream was prepared and treated with basic ion exchange resins to separate phenol impurities. The feed stream comprised about 47% methyl benzyl alcohol, 15% acetophenone, 34% ethyl benzene as well as 1000–14000 ppm phenol and phenol derivatives. The resins employed were poly(vinylpyridine) resin (Reillex 425 resin from Reilly Industries, Inc.) and strongly basic styrene divinyl benzene quaternary ammonium anion exchange resin (Amberlyst A-26 from Rohm and Haas). In the case of this latter resin, the copolymer was chloromethylated and then aminated with trimethyl amine; the functional structure is $-N(CH_3)_3{}^+Cl^-$.

The feed stream was passed through a column packed with the resin at a flow rate of 0.3 to 1.5 gallons per minute per cubic foot of resin. Temperature was 20° to 40° C. The following table shows the results obtained.

TABLE 1

| Run | Type of Resin | Feed Phenols Content, ppm | Flow Rate gal/min/ft$^3$ of Resin | % Phenols removal |
|---|---|---|---|---|
| 1 | Amberlyst A-26 | 1060 | 0.43 | 70.7 |
| 2 | Reillex 425 | 1060 | 0.30 | 42.5 |
| 3 | Reillex 425 | 1360 | 0.32 | 30.0 |

These results show that the resin treatment was effective in reducing the phenols content. The Amberlyst resin was more effective for removing phenols. The treated methyl benzyl alcohol stream is oxidized with molecular oxygen to form hydrogen peroxide as described in Example 1.

EXAMPLE 3

The synthetic oxidation feed from Example 2 was caustic treated to remove phenols. About 100 g of the feed were contacted at 32° C. with 20 g 5% aqueous caustic, and the resulting mixture was separated into aqueous and organic phases. Phenols removal from the organic stream was 95%. The treated methyl benzyl alcohol stream is oxidized with molecular oxygen to form hydrogen eroxide as described in Example 1.

We claim:

1. In a process for the production of hydrogen peroxide from methyl benzyl alcohol contaminated with organic phenol impurities which inhibit hydrogen peroxide formation, the improvement which comprises treating the contaminated methyl benzyl alcohol to remove the said phenol impurities or to convert the said phenol impurities to non-inhibiting materials, and thereafter reacting the treated methyl benzyl alcohol with molecular oxygen to form hydrogen peroxide.

2. The process of claim 1 wherein the said organic phenol impurities are removed from said methyl benzyl alcohol by distillation.

3. The process of claim 1 wherein the said organic phenol impurities are removed from said methyl benzyl alcohol by caustic treatment.

4. The process of claim 1 wherein the said organic phenol impurities and removed from said methyl benzyl alcohol by ion exchange resin treatment.

5. The process of claim 1 wherein the said organic phenol impurities are removed from said methyl benzyl alcohol by distillation and caustic or ion exchange resin treatment.

6. The process of claim 1 wherein said organic phenol impurities are selected from the group consisting of phenol and ethyl phenols.

* * * * *